(12) United States Patent
Hansen et al.

(10) Patent No.: US 6,423,346 B1
(45) Date of Patent: Jul. 23, 2002

(54) FISH GELATINOUS COMPOSITION FOR USE AS AN INGREDIENT IN TABLETS

(75) Inventors: Morten Mohr Hansen, Allerød; Per Vilstrup, Farum; Nina Musaeus Jensen, Hellerup, all of (DK)

(73) Assignee: BASF Health & Nutrition A/S, Ballerup (DK)

( * ) Notice: Subject to any disclaimer, the term of this patent is extended or adjusted under 35 U.S.C. 154(b) by 0 days.

(21) Appl. No.: 09/379,790

(22) Filed: Aug. 24, 1999

Related U.S. Application Data

(60) Provisional application No. 60/098,179, filed on Aug. 26, 1998.

(30) Foreign Application Priority Data

Aug. 25, 1998 (DK) .......................... 1998 01065

(51) Int. Cl.[7] .......................... A61K 35/12; A61K 9/64; A61K 9/20; A01N 31/04
(52) U.S. Cl. .......................... 424/520; 424/456; 424/460; 424/464; 424/489; 424/492; 512/725
(58) Field of Search .......................... 424/456, 520, 424/464, 460, 489, 492; 514/54, 725; 536/2, 3, 119, 123.1

(56) References Cited

U.S. PATENT DOCUMENTS

| 2,824,807 A | | 2/1958 | Laster et al. |
|---|---|---|---|
| 4,519,961 A | | 5/1985 | Schumacher et al. |
| 4,670,247 A | | 6/1987 | Scialpi |
| 4,892,889 A | | 1/1990 | Kirk et al. |
| 5,478,569 A | | 12/1995 | Berneis et al. |
| 5,603,952 A | | 2/1997 | Soper |
| 5,767,107 A | * | 6/1998 | Chaundy et al. |

FOREIGN PATENT DOCUMENTS

| EP | 0 346879 | 12/1989 |
|---|---|---|
| EP | 0 347751 | 12/1989 |
| GB | 1200906 | 8/1970 |
| WO | 96/20612 | 7/1996 |

OTHER PUBLICATIONS

Seafood Saf., Process., Biotechnol. (19), pp 187–197. Lu et al. Characterization of several fish gelatins, 1997.*

* cited by examiner

*Primary Examiner*—Christopher R. Tate
*Assistant Examiner*—Michele Flood
(74) *Attorney, Agent, or Firm*—Finnegan, Henderson, Farabow, Garrett & Dunner, L.L.P.

(57) ABSTRACT

Particulate composition comprising one or more physiologically active substances and a fish gelatinous protective colloid containing at least 50% by weight of fish gelatin, wherein the fish gelatin is at least partly composed of fish gelatin having a bloom strength of above 100, and wherein the composition is obtainable by a particle forming spraying or double emulsifying method.

9 Claims, No Drawings

FISH GELATINOUS COMPOSITION FOR USE AS AN INGREDIENT IN TABLETS

This application claims priority of Provisional Application No. 60/098,179, filed Aug. 26, 1998, the contents of which are incorporated herein by reference.

The present invention relates to a particulate composition comprising one or more physiologically active substances and a gelatinous protective colloid.

Physiologically active substances are enclosed in protective colloids, such as gelatines, i.a. to protect them from influences inflicted during storage, transport, handling and use, e.g. influences from oxygen, moisture and light radiation and physical influences, in order to avoid physical and chemical decomposition of the substance. Furthermore, a protective colloid may be used to prevent the active substance from reacting with other substances present in the composition or with substances with which it may come into contact during use. Also, a protective colloid is used to transform liquids and other substances, which are difficult to handle and process, e.g. due to stickiness, into a solid form suitable for handling and processing during use, such as a powder of microcapsules.

Fish gelatine (also known as fish gelatin) is used for dietary applications, where mammalian gelatines are unacceptable on religious grounds. Fish gelatine is available as Kosher grade.

EP-A1-0 346 879 discloses a composition comprising a solid particulate water insoluble drug coated with a solid fish gelatine coating, wherein the composition is produced by simple coacervation of the fish gelatine. The fish gelatine is soluble at 5–10° C.

WO 96/20612 discloses a method of forming microencapsulated food or flavor capsules as well as capsules produced by the method. The method includes forming a mixture of a warm water fish gelatine and the food or flavor particles in aqueous media, and microencapsulating the particles with the gelatine at a temperature above 16–27° C. by complex coacervation to form microencapsulated capsules, and optionally separating the capsules. Preferably, the warm water fish gelatine used has a bloom of from about 150 to about 300.

Simple and complex coacervation techniques require the use of relatively low concentration solutions of gelatine, and hence the particles formed from the solutions have a relatively high content of water, which is difficult and expensive to remove. Both dried and non-dried particles produced by coacervation have a low ability to resist mechanical influences.

GB-1 200 906 discloses a process for preparing a composition in dry, particulate, free-flowing form and comprising cold water soluble or dispersable gelatine and fat-soluble vitamins, the process comprising partially hydrolysing a gelatine solution by treatment with base or acid at a temperature of 40 to 95° C., neutralising the gelatine solution and finely dispersing therein the fat-soluble vitamin or vitamins, comminuting the emulsion to particles and solidifying the particles. The starting gelatine may be low or high bloom gelatin.

U.S. Pat. No. 4,670,247 discloses a process for preparing fat-soluble vitamin beadlets including forming an aqueous emulsion of a fat-soluble vitamin-active material and a protective colloid comprising gelatine and a reducing sugar, and converting said emulsion to a dry particulate form, wherein the dry particulate form is subjected to heat treatment in order to obtain a cross-linking between the sugar and the gelatine molecules. The gelatine may be any gelatine having bloom of between about 0 and 300.

EP-B1-0 347 751 discloses a stable, cold water-dispersable powder preparation of fat-soluble substances, which are enveloped in a protective colloid in the form of fish gelatine. The fish gelatine used is "Norland HiPure Liquid Gelatin", which is a zero bloom gelatine.

The prior art fish gelatinous compositions may be used as additives for a wide range of foods. However, the prior art compositions suffer from the drawback that they are not suitable for use as an ingredient in tablets, since particles formed have insufficient strength to resist the mechanical influence to which it is subjected during tabletting.

U.S. Pat. No. 4,892,889 discloses a process for making a directly-compressible vitamin powder utilising a conventional spray-drying method. The process comprises the steps of (A) combining a fat-soluble vitamin, a gelatin having a bloom number between 30 and 300, a water-soluble carbohydrate, and water to form a mixture, and (B) spray-drying the mixture in a conventional spray-drier to form a powder, wherein the content of carbohydrate is sufficient to prevent extrusion of the vitamin.

U.S. Pat. No. 2,824,807 discloses a method of spray drying solutions of gelatine containing e.g. vitamins comprising the steps of atomising the solution in a cool air zone at a temperature of 0–200° F. to form droplets and drying of the droplets in a drying zone at a temperature of 250–1000° F. to effect solidifying of the droplets.

U.S. Pat. No. 4,519,961 discloses a process for pulverising substances, which are sensitive to oxidation, e.g. vitamins, comprising the steps of providing a dispersion of the oxidation-sensitive substance in an aqueous solution containing a film-forming colloid and a saccharides atomising said dispersion within the spraying zone of a spraying tower to form discrete particles while contacting the particles with a hydrophobic spraying assistant at a temperature, at which the colloid does no solidify/gelatinise, and drying the particles laden with the spraying assistant in a fluid bed to solidify them.

Thus, the technical problem addressed by the present invention is to provide a gelatinous composition, which is Kosher acceptable, and which is suitable for use as an ingredient in tablets.

The said technical problem is solved by the particulate composition of the invention comprising one or more physiologically active substances and a fish gelatinous protective colloid containing at least 50% by weight of fish gelatine, wherein the fish gelatine is at least partly composed of fish gelatine having a bloom strength of above 100, and wherein the composition is obtainable by a particle forming spray congelation method or a double emulsifying method.

It has surprisingly been found that particles, which are prepared using fish gelatine having a bloom strength of above 100 and using as a particle forming method either a spray congelation method or a double emulsifying method, have physical properties with respect to resistance to mechanical influences, such as pressure, shear force and impact, which are far superior to those of the prior art particles.

Thus, the present invention is based on the recognition that it is possible to produce a fish gelatinous composition with high mechanical strength, and that such a high strength composition may be used as an ingredient in tablets, such as nutritional supplement tablets. Therefore, the present invention has provided a possibility or producing tablets containing physiologically active substances protected by fish gelatine.

Furthermore, the present invention has provided a possibility of producing a Kosher and Halal acceptable composition for use as an ingredient in tablets.

When the mechanical strength of gelatinous particles is insufficient to resist the mechanical influences inflicted during tabletting, the particles will decompose leading to extrusion of the active substance. Such extrusion results in discolouring of the tablets, which is not acceptable. Also, such extrusion leads to the decomposition of the active substance, especially if the active substance is sensitive to oxidation or may react with other ingredients of the tablets.

A further advantage of the composition of the present invention is that the technical problems of discolouring of the tablets made therefrom and oxidation of the active substance may be avoided.

Moreover, it has further been shown that the particulate composition of the invention has improved storage stability compared to prior art products. It is believed that this fact is also due to the improved mechanical strength of the particles resulting in a reduced degradation of the active ingredient during storage.

In a preferred embodiment of the invention the fish gelatinous protective colloid contains at least 70% by weight, preferably at least 90% by weight, of fish gelatine.

In a preferred embodiment of the invention, the fish gelatine contains at least 50% by weight, more preferably at least 70% by weight, and most preferably at least 90% by weight, of fish gelatine having a bloom strength of above 100.

The fish gelatinous protective colloid may consist entirely of fish gelatine having a bloom strength of above 100 or it may be a mixture of such a fish gelatine and any other fish gelatine including a gelatine having a bloom strength of below 100. The fish gelatines, regardless of bloom strength, may be partly hydrolysed.

In a preferred embodiment of the invention the fish gelatine has a bloom strength of 100–300, preferably 120–300, more preferably 140–300, more preferably 160–280, more preferably 180–260, and most preferably 200–240.

Preferably, the fish gelatine has a gelation temperature of 10–30° C., more preferably 11–29° C., more preferably 12–28° C., more preferably 13–27° C., more preferably 14–26° C., more preferably 14–24° C., more preferably 15–23° C., more preferably 16–22° C., and most preferably 17–21° C.

In addition to the fish gelatine, the fish gelatinous protective colloid may comprise exudates, such as gum arabic, tragacanth, gum karaya and gum ghatti; extracts from seaweed, such as agar, alginate, carrageenan and furcellaran; extracts from plants, such as pectin, arabinogalactan and vegetable proteinaceous hydrocolloids; extracts from marine and terrestrial animals, such as kosher gelatines, casein and caseinate; flours from seeds, such as guar, locust bean and soya bean; proteins from seeds, such as soya bean protein; flours from cereals, such as starches and microcrystalline cellulose; biosynthetic or fermentation derived hydrocolloids, such as dextran, xanthan, and curdlan; chemically modified hydrocolloids, such as cellulose derivatives, including methyl cellulose, carboxymethylcellulose and hydroxypropyl-cellulose, and other derivatives, including modified starches and low methoxyl pectin; synthetic hydrocolloids, such as polyvinyl pyrrolidon, polyvinyl alcohol, carboxyvinyl polymers etc. Also reference is made to R. A. Morton, "Fat Soluble Vitamins", Intern. Encyclopedia of Food and Nutrition, Vol. 9, Pergamon Press, pp. 128–131, 1970, which is included herein by this reference. Preferred additional colloids included in the fish gelatinous protective colloid are gum arabic, vegetable proteinaceous hydrocolloids, kosher gelatines, casein, caseinate, soya bean protein, modified starches and mixtures thereof.

In addition to the function as protective agent the fish gelatinous protective agent also functions as an emulsifier. However, the composition of the invention may comprise further emulsifiers, e.g. ascorbyl palmitate, mono- and diglycerides of fatty acids and derivatives thereof, and lecithin.

The composition of the invention may include further components conventionally used in gelatinous compositions, such as antioxidants, e.g. t-butylhydroxyloluene (BHT), t-butylhydroxyanisole (BRA), ascorbic acid, ascorbyl palmitate, sodium ascorbate, tocopherols, TBHQ, ethoxyquine, propyl gallate, and extracts from herbs, i.a. rosemary extract; powdering agents, e.g. starches, modified starches, tri-calcium phosphate, lactose, mannitol, ethylcellulose, coagulated albumin, hardened gelatine, casein, stearat-Ca, stearat-Na, metal soaps, hydrogenated ricinus oil, polyoxide, talcum, waxes and silicates; anti-caking agents, e.g. tri-calcium phosphate and silicates, i.a. silicon dioxide and sodium aluminium silicate; plasticisers, e.g. carbohydrates and carbohydrate alcohols, examples of which are saccharose, glucose, fructose, lactose, invert sugar, sorbitol, mannitol, maltodextrin, glycerin and mixtures thereof, preferably saccharose, lactose, maltodextrin and mixtures thereof.

Following gelation, the fish gelatine of the composition of the invention may he cross-linked, which may be obtained by thermal and/or chemical treatment of the gelatine in the presence of a carbohydrate or an aldehyde or a combination thereof, and/or by enzymatic treatment. The cross-linking may be carried out by any conventional method therefore.

Fish gelatine having a bloom strength of above 100 originates from a wide variety of warm water fish, e.g. tuna and tilapia. Examples of suitable commercial products are gelling fish gelatines from Croda Colloids Ltd., England, and ROUSSELOT® FG, e.g. ROUSSELOT ® 200 FG 30 from, SKW Biosystems, France.

The physiologically active substances of the present invention may be any substance, which during storage, transport, handling and use requires protection, e.g. from oxygen, moisture, light radiation, and physical influences, in order to avoid physical and chemical decomposition of the substance. Furthermore, a protective colloid may be used to prevent the active substance from reacting with other substances present in the composition or with substances with which it may come into contact during use. Also, a protective colloid is used to transform liquids and other substances, which are difficult to handle and process, e.g. due to stickiness, into a solid form suitable for handling and processing during use, such as a powder of microcapsules.

Examples of physiologically active substances suitable for use in the present invention are fat-soluble substances, such as vitamins, fatty acids, e.g. mono- and polyunsaturated fatty acids, which may be added in the form of fish oil containing i.a. the (n-3) fatty acids docosahexaenoic acid (DHA) and eicosapentaenoic acid EPA), and in the form of evening primrose oil and castor oil containing i.a. the (n-6) fatty acid γ-linolenic acid, carotenoides, e.g. β-caroten, lutein, lycopene, β-cryptoxanthin and zeaxanthin, oils and fats; water-soluble substances, such as vitamin C; enzymes, e.g. amylase; pharmaceuticals, such as griseofulvin, ibuprofen, benzodiazepines, phenacetin, hormones and paracetamol; and other nutritional supplements, such as minerals.

The composition of the invention has the form of particles, such as a powder of microcapsules. The particles have the structure of a continuous matrix of the fish gelatinous protective colloid enclosing a number, usually several, cores of physiologically active substances. The particulate composition of the invention is preferably free-flowing.

The present invention further relates to a process for preparing a particulate fish gelatinous composition, the process comprising the steps of providing an aqueous solution of a fish gelatinous protective colloid at a temperature of above the gelation temperature or the said colloid, the said colloid containing at least 50% by weight of fish gelatine, which is at least partly composed of fish gelatine having a bloom strength of above 100, adding to the said solution one or more physiologically active substances to obtain an aqueous mixture, subjecting the aqueous mixture to a spray congelation method or a double emulsifying method to transform the aqueous mixture to particles and to effect a gelation of the particles by cooling them to a temperature of below their gelation temperature to obtain gelled particles, and removing any excess water from the gelled particles to obtain dried particles.

The particles prepared with the method of the invention has improved mechanical strength compared to the prior art particles.

In both a spray congelation method and a double emulsifying method, a gelation of the particles formed is effected by lowering the temperature to below their gelation temperature. This is contrary to other types of spraying processes, such as conventional spray drying, wherein the droplets formed in the spraying are not gelatinised but solidified by drying. It is believed that such a gelation of the particles contribute to the improvement of the mechanical strength of the particles obtained with the method of the invention.

Any water soluble additional ingredient is preferably dissolved together with the gelatin. Alternatively, additional ingredients are added together with the physiologically active substance.

The removal of any excess water may be carried out by any conventional method therefore, such as filtration, tray drying, fluid bed drying, preferably in Combination with the spray congelation method in a suitable spraying tower. Drying in a fluid bed is preferred.

Spray Congelation

In connection with the present invention the expression "a spray congelation method" includes any spraying technique, wherein the particles formed in the spraying are substantially gelatinised by lowering of the temperature to below the gelation temperature of the particles prior to drying.

The spraying method may be carried out using any conventional equipment therefore, e.g. rotary atomisers, pressure nozzles, pneumatic nozzles and sonic nozzles.

In a spray congelation process, a suspension containing a hydrocolloid having a temperature higher than the gelling/melting point of the emulsion, i.e. from about 30° C. to about 95° C., and a viscosity of preferably between 50 and 600 mpa.s, is preferably sprayed using an atomizing nozzle or an atomizing wheel into a spraying chamber, wherein the temperature is from 0° to about 40° C., thereby forming microcapsules of gelatinised hydrocolloid.

A powdery spraying excipient is preferably blown into the spraying chamber in order to prevent agglomeration of the gelatinized microcapsules and to prevent adherence to the chamber wall. The spraying excipient is preferably supplied in an amount of from 0.5 to 50 percent by weight based on the weight of the final product.

The microcapsules are transferred to a fluid bed, wherein they may be dried to a residual water content of between 0 and 10% (preferably from 2 to 5%) and in which excessive spraying excipient is separated. The drying air temperature is preferably from about 0° to about 6° C.

Double Emulsifying Method

In connection with the present invention, the expression "double emulsifying method" means any method comprising the steps of forming a first, aqueous mixture of gelatine and a physiologically active substance, distributing the said first aqueous mixture as particles in a water immiscible medium to form a second mixture, and cooling the second mixture to a temperature of below the gelation temperature of the particles. The distribution of the first, aqueous medium in the water immiscible medium may be carried out by any conventional method therefore, such as spraying, stirring and liquid stream catch. The water immiscible medium may e.g. be mineral oil, castor oil or propylene glycol.

The present invention further relates to a tablet comprising conventional excipients and a composition comprising one or more physiologically active substances and a gelatinous protective colloid. The tablet of the invention is characterized in that the gelatinous protective colloid contains at least 50% by weight of fish gelatine, which is at least partly composed of fish gelatine hating a bloom strength of above 100, and that the composition is obtainable by a particle forming spray congelation method or a double emulsifying method.

Definitions

As used herein the expression "gelation temperature" means setting point as determined by the test method BS 757:1975, item 10. In the said standard test a 10% solution of air dry gelatine is cooled from. 45° C. to 20° C. If the gelation temperature of the gelatine to be tested is less than 20° C., the temperature is of course lowered until gelation is observed.

In connection with the present invention the expression "bloom strength" means gel strength as determined in the test method BS 757:1975, item 7.

The expression aqueous mixture means an aqueous solution, emulsion or suspension.

In the following the invention will be described in further detail with reference to the examples.

METHODS

Extractability of Vitamin A before Compression

Principle:

A microcapsule powder containing Vitamin A as active substance is contacted with ether to extract active substance, and the amount extracted is determined by spectrophotometry. The total amount of active substance in the microcapsules is also determined by dissolving the microcapsules in water by heating, extracting the active substance with ether and measuring the content of active substance by spectrophotometry. Results are expressed as the ratio of extracted active substance to total active substance. The level of active substance, which may be extracted from the microcapsule powder, expresses the ability of the microcapsules to protect the active substance.

Procedure:

1. Approximately 1 g of Vitamin A-containing microcapsule powder is weighed (2 decimals) and transferred quantitatively to a 100 ml measuring flask.

2. Approximately 50 ml ether is added, and the flask is shaken 2 minutes by hand. The flask is filled with ether to the 100 ml mark and the content of the flask is mixed, The solution is allowed to settle for 5 minutes.

3. A sample is taken from the solution, and the extinction at 326 nm (maximum) is measured using isopropanol as a reference. The extinction should be in the range of 0.200 to 0.900. If this is not the case, the sample is diluted with isopropanol and measured again. In case of dilution, the measurement should be made within minutes from the dilution with isopropanol.

Extractability of Vitamin A after Compression

Principle:

A microcapsule powder containing Vitamin A as active substance is subjected to a certain pressure in a predetermined period of time to produce a tablet. The tablet is contacted with ether to extract active substance, and the amount extracted is determined by spectrophotometry. The total amount of active substance in the microcapsules is also determined by dissolving the microcapsules in water by heating, extracting the active substance with ether and measuring the content of active substance by spectrophotometry. Results are expressed as the ratio of extracted active substance to total active substance. The level of active substance, which may be extracted from the tablet, expresses the ability of the microcapsules to protect the active substance following a compression step.

Procedure:

1. Approximately 0.2 g of Vitamin A-containing microcapsule powder is weighed and placed in a cell between two pistons and subjected to a pressure of 1250 bar for five seconds to form a tablet.

2. The tablet is transferred to a weighed paper, weighed. (4 decimals)and transferred quantitatively to a 200 ml measuring flask.

3. Approximately 100 ml petroleum ether is added, and the flask is subjected to sonification for 10 minutes. The flask is filled with petroleum ether to the 200 ml mark and the content of the flask is mixed. The solution is allowed to stand for 5 minutes.

4. A 5 ml sample is taken from the solution and diluted with isopropanol to a concentration of approx. 10 IU Vitamin A/ml, and the extinction at 326 nm (maximum) is measured using isopropanol as a reference. The extinction should be in the range of 0.200 to 0.900. If this is not the case, the sample is further diluted with isopropanol and measured again. The measurement should be made within 15 minutes of the dilution with isopropanol,

COMPARATIVE EXAMPLE 1

2438 grams of fish gelatine (Norland Dry Non Gelling Fish Gelatine, lot # 7154 NGKD, 0 bloom, from Norland Products Inc., USA) and 2976 grams of saccharose was dissolved in 4.0 l demineralized water at 65° C. in an emulsion tank. A mixture of 2000 grams of Vitamin A Acetate 2.8 million IU/g and 140 g t-butyl hydroxytoluene (BHT) was heated to 65° C. in a beaker. The oily mixture was added to the aqueous solution of gelatine and saccharose under slow agitation, which was then vigorously agitated for 40 minutes at 65° C. Then the final emulsion was diluted with 2.75 l demineralized water to a viscosity of 168 cP. The mean oil droplet size was measured to be 0.28 μm.

Subsequently the emulsion was atomized in a spray tower, where the droplets were covered with starch and dried. Only part of the emulsion was sprayed. This yielded after screening on mesh 30/120 approx. 1 kg of a particulate product with a potency of 570,000 IU/g, an extractability before compression of 0.1% of the total Vitamin A content and an extractability after compression of 35.6% of the total vitamin A content.

COMPARATIVE EXAMPLE 2

2438 grams of fish gelatine (200 bloom, Rousselot 200 FG; 30 from SKW Biosystems, France) and 2976 grams of saccharose were dissolved in 6.0 l demineralized water at 65° C. in an emulsion tank and stored overnight to remove trapped air bubbles. A mixture of 2000 grams of Vitamin A Acetate 2.8 million IU/g and 140 g bytulated hydroxytoluene (BHT) was heated to 65° C. in a beaker. The oily mixture was added to the aqueous solution of gelatine and saccharose under slow agitation/ which was then vigorously agitated for 40 minutes at 65° C. Then the final emulsion was diluted with 1.5 l demineralized water to a viscosity of 164 cF. The mean oil droplet size was measured to be 0.29 μm.

Subsequently, the emulsion was atomized in a spray tower, where the droplets were covered with starch and dried. Only part of the emulsion was sprayed. This yielded after screening on mesh 30/120 approx. 1 kg of a particulate product with a potency of 552,000 IU/g, an extractability before compression of 0.1% of the total Vitamin A content and an extractability after compression of 29.5% of the total vitamin A content.

EXAMPLE 3

2438 grams of fish gelatine (200 bloom, from Croda Colloids Ltd., UK) and 2976 grams of saccharose were dissolved in 5.0 l demineralized water at 65° C. in an emulsion tank and stored overnight to remove trapped air bubbles. A mixture of 2000 grams of Vitamin A Acetate 2.8 million IU/g and 140 g t-butyl hydroxytoluene (BHT) was heated to 65° C. in a beaker. The oily mixture was added to the aqueous solution of gelatine and saccharose under slow agitation, which was then vigorously agitated for 40 minutes at 65° C. Then the final emulsion was diluted with 2.45 l demineralized water to a viscosity of 172 CP. The mean oil droplet size was measured to be 0.29 μm. Subsequently the emulsion was atomized in a spray tower, where the droplets were covered with starch and dried. Only part of the emulsion was sprayed. This yielded after screening on mesh 30/120 approx. 1 kg of a particulate product with a potency of 593,000 IU/g, an extractability before compression of 0.1% of the total Vitamin A content and an extractability after compression of 7,9% of the total vitamin A content. As will appear from the results the extractability after compression of the composition of the invention is far superior to that of the prior art composition of Comparative Example 1 and 2.

EXAMPLE 4

2438 grams of fish gelatine (200 bloom, Rousselot 200 FG 30 from SKW Biosystems, France) and 2976 grams of saccharose were dissolved in 5.0 l demineralized water at 65° C. in an emulsion tank and stored overnight to remove trapped air bubbles. A mixture of 2000 grams of Vitamin A Acetate 2.8 million IU/g and 140 g t-butyl hydroxytoluene (BHT) was heated to 65° C. in a beaker. The oily mixture was added to the aqueous solution of gelatine and saccharose under slow agitation, which was then vigorously agitated for 40 minutes at 65° C. Then the final emulsion was diluted with 3.5 l demineralized water to a viscosity of 168 cP. The mean oil droplet size was measured to be 0.29 μm. Subsequently the emulsion was atomized in a spray tower, where the droplets were covered with starch and dried. Only part of the emulsion was sprayed. This yielded after screening on mesh 30/120 approx. 1 kg of a particulate product with a potency of 584,000 IU/g, an extractability before compression of 0.1% of the total Vitamin A content and an extractability after compression of 12,1% of the total vitamin A content. As will appear from the results the extractability after compression of the composition of the invention is far superior to that of the prior art composition of Comparative Example 1 and 2.

EXAMPLE 5

2250 grams of fish gelatine (200 bloom, Rousselot 200 FG 30 from SKW Biosystems, France) and 3375 grams of saccharose were dissolved in 5.0 l demineralized water at 65° C. in an emulsion tank and stored overnight to remove trapped air bubbles. A mixture of 1500 grams of Vitamin A Palmitate 1.7 million IU/g and 93 g dl-α-tocopherol was heated to 65° C. in a beaker. The oily mixture was added to the aqueous solution of gelatin and saccharose under slow agitation, which was then vigorously agitated for 40 minutes at 65° C. Then the final emulsion was diluted with 4.55 l demineralized water to a viscosity of 168 cP. The mean oil droplet size was measured to be 0.29 μm. Subsequently the emulsion was atomized in a spray tower, where the droplets were covered with starch and dried. Only part of the emulsion was sprayed. This yielded after screening on mesh 30/120 approx. 1 kg of a particulate product with a potency of 287,000 IU/g, an extractability before compression of 0.04% of the total Vitamin A content and an extractability after compression of 11,4% of the total vitamin A content. As will appear from the results the extractability after compression of the composition of the invention is far superior to that of the prior art composition of Comparative Example 1 and 2.

What is claimed is:

1. A particulate composition comprising one or more physiologically active substances and a fish gelatinous protective colloid containing at least 50% by weight of fish gelatine, and, optionally, a second hydroccolloid; wherein the fish gelatin contains at least 50% by weight of fish gelatin having a bloom strength of above 100, and wherein the composition is obtained by a particle forming spray congelation method or a double emulsifying method.

2. A composition according to claim 1, wherein the fish gelatinous protective colloid contains at least 70% by weight of fish gelatin.

3. A composition according to claim 2, wherein the fish gelatinous protective colloid contains at least 90% by weight of fish gelatin.

4. A composition according to any one of claim 1, 2, or 3, wherein the second hydrocolloid is selected from the group consisting of gum arabic, vegetable proteinaceous hydrocolloids, kosher gelatines, casein, caseinate, soya bean protein, and modified starches.

5. A composition according to claim 1, whereas the fish gelatine contains at least 70% by weight of fish gelatin having a bloom strength of above 100.

6. A composition according to claim 1, wherein the fish gelatin has a bloom strength of 180–260.

7. A composition according to claim 1, wherein the fish gelatin has a gelation temperature of 15–25° C.

8. A process for preparing a particulate fish gelatinous composition, the process comprising the steps of: providing an aqueous solution of a fish gelatinous protective colloid at a temperature of above the gelation temperature of the colloid, the colloid containing at least 50% by weight of fish gelatin and, optionally a second hydrocolloid wherein the fish gelatin contains, at least 50% by weight of fish gelatin having a bloom strength of above 100; adding to the solution one or more physiologically active substances to obtain an aqueous mixture; subjecting the aqueous mixture to a spray congelation method or a double emulsifying method to transform it to particles and to effect a gelation of the particles by cooling them to a temperature of below their gelation temperature to obtain gelled particles; and removing any excess water from the gelled particles to obtain dried particles.

9. A tablet comprising conventional excipients and a particulate composition therein, whereby the particulate composition contains one or more physiologically active substances and a gelatinous protective colloid, wherein the gelatinous protective colloid contains at least 50% by weight of fish gelatin, and, optionally a second hydrocolloid, wherein the fish gelatin contains at least 50% by weight of fish gelatin having a bloom strength of above 100, and wherein the composition is obtained by a particle forming spray congelation method or a double emulsifying method.

* * * * *